United States Patent [19]

Hon

[11] 4,320,764
[45] Mar. 23, 1982

[54] FETAL ELECTRODE
[75] Inventor: Edward H. Hon, Bradbury, Calif.
[73] Assignee: American Home Products Corporation, New York, N.Y.
[21] Appl. No.: 159,113
[22] Filed: Jun. 13, 1980
[51] Int. Cl.³ .............................................. A61B 5/00
[52] U.S. Cl. .................................. 128/635; 128/642
[58] Field of Search ............... 128/635, 639, 642, 784, 128/785, 631

[56] References Cited

U.S. PATENT DOCUMENTS

| | | | |
|---|---|---|---|
| 2,168,867 | 8/1939 | George | 128/635 |
| 3,827,428 | 8/1974 | Hon et al. | 128/642 |
| 3,923,627 | 12/1976 | Niedrach et al. | 128/635 |
| 3,973,555 | 8/1976 | Möller | 128/635 |
| 4,252,124 | 2/1981 | Maurer et al. | 128/642 |

FOREIGN PATENT DOCUMENTS 2749048  5/1979  Fed. Rep. of Germany ...... 128/642

Primary Examiner—William E. Kamm
Attorney, Agent, or Firm—Eugene L. Flanagan, III

[57] ABSTRACT

Apparatus for use in measuring continuously the change in pH values of a fetus, comprises a holder made of an insulating material, a spiral electrode extending from the forward end of said holder and adapted to engage the fetus during delivery, a maternal electrode supported on said holder rearward of said spiral electrode, said electrodes including a material which forms a half cell in the presence of hydrogen ions, and means responsive to the potential difference across said first and second electrodes for continuously measuring the changes in pH of the fetus.

7 Claims, 2 Drawing Figures

FETAL ELECTRODE

This invention relates to an electrode for use in continuously measuring changes in hydrogen ion concentration of a fetus during birth.

DESCRIPTION OF THE PRIOR ART

The pH value of blood is related largely to the carbon dioxde and fixed acid concentration in the blood. For many years it has been recognized that the pH value of the blood (or tissue) of a fetus during delivery may provide an early indication of fetal distress since increased carbon dioxide with or without fixed acid concentration (manifested by decreasing pH values) may mean that the fetus is receiving insufficient oxygen, for example, because of compression of the umbilical cord. If not corrected, conditions which restrict oxygen supply can, and do cause permanent brain damage.

Although the need to monitor fetal pH values continuously has long been recognized, there are currently no satisfactory devices available for this purpose. Accordingly, fetal pH is monitored by sampling the blood at preselected intervals (about 20 minutes) and measuring the pH value of each of the samples. However, severe fetal distress can easily occur between sampling times, and it is impractical to reduce the sampling period to the extent required for effective monitoring.

It is conventional practice to monitor continuously pH values for industrial and other purposes, and efforts have been made to adapt known pH electrodes for the purpose of continuously monitoring the pH values of a fetus. Typically, pH values are measured using two electrochemical half cells with the potentials across the half cells connected in opposition so as to cancel each other. One half cell serves as a reference and the other as a measuring cell. If the measuring cell is subjected to hydrogen ions from a test solution it is possible to measure only the potential resulting from ionic conduction from the test solution. This potential can then be converted into an accurate indication of pH value.

A description of a conventional ion selective glass electrode (the most common pH electrode) may be found in U.S. Pat. No. 3,959,107 of Horner, columns 1 and 2. This patent describes some of the problems involved in manfacturing pH electrodes with the reference and measuring cells combined into a composite structure, and the steps taken to prevent contamination from other than the desired ionic flow.

Moller et al. U.S. Pat. No. 3,973,555 discloses a composite pH electrode for use in continuously monitoring the pH values of a fetus. In this patent, a glass electrode includes reference and measuring electrodes in suitable electrolytes. The tip of the electrode is made of a pH sensitive material (i.e., a glass membrane) across which the desired ionic conductivity exists.

The Moller electrode is a fairly expensive and difficult device to manufacture. More important, however, it is inherently slow, taking as much as 40 seconds to respond to a material change in pH value. When measuring the pH of a fetus, a delay of this order of magnitude can be significant. Moreover, for obvious reasons, it is extremely undesirable to attempt to insert the tip of a glass tube or needle into a fetus during birth.

OBJECTS OF THE INVENTION

The main object of this invention is to provide an electrode which can be used to monitor continuously changes in pH values of a fetus.

A more specific object is to provide an electrode of the type described which has a substantially shorter response time than the Moller electrode.

A further object of the invention is to provide a fetal electrode for measuring changes in hydrogen ion concentration, which is relatively inexpensive to manufacture, which is easy to apply, and which minimizes any likelihood of injury to the fetus.

SUMMARY OF THE INVENTION

In accordance with the invention, a fetal pH electrode assembly comprises a holder made of an insulating material from which fetal and maternal electrodes extend. The electrodes are each made of a solid material sensitive to hydrogen ions thereby forming two half cells, and the fetal electrode is adapted to be inserted into the fetal tissue. Means responsive to the difference between the voltages produced by the two half cells measures continuously the change in hydrogen ion concentration (pH) of the fetus.

IN THE DRAWINGS

FIG. 1 shows the electrode assembly in accordance with a preferred embodiment of the invention; and FIG. 2 shows diagrammatically a block diagram of the measuring circuit used to monitor changes in pH values and fetal heart rate.

DETAILED DESCRIPTION

In the past, measurement of fetal pH has involved the accurate measurement of absolute values. The electrode of the invention may or may not measure accurately absolute pH values, but the invention is based in part on the recognition that absolute values are relatively unimportant since it is changes in hydrogen ion concentration which reflect momentary fetal condition. Accordingly, it is not necessary to maintain an exact reference level in order to monitor fetal pH values as an indicator of fetal well-being.

Electrodes sensitive to hydrogen ions may generally be sensitive as well to chloride (and possibly oxygen) ions which exist in the fetal environment. The invention also relies in part on the recognition that the concentration of chloride ions in the uterine fluids and in the fetal tissue will remain relatively constant during the course of labor. This is not to say that the concentration of chloride ions will necessarily be the same in both places although this, also, may or may not be the case. However, if the concentration of chloride ion remains constant with time, then any potential difference across the elctrodes may correctly be assumed to be the result of a change in the concentration of hydrogen ions and, therefore, representative of pH changes. This means that it is not necessary to use a glass membrane (or the like) sensitive only to hydrogen ion concentration to measure changes in pH.

Figure 1:
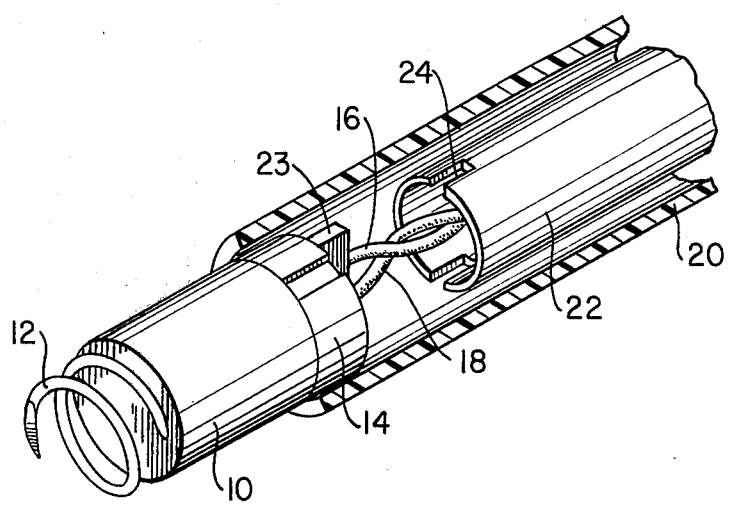
Figure 2:
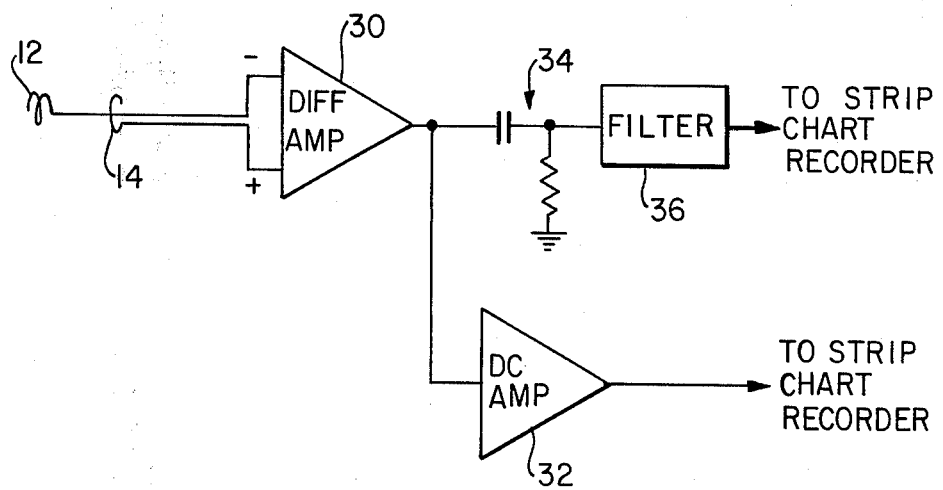

Referring now to FIG. 1, an electrode assembly capable of monitoring both fetal heart rate and changes in hydrogen ion concentration is shown. Mechanically, the device is simple and includes a cylindrical holder 10, made of an insulating material, on which a forward spiral electrode 12 and a rear maternal electrode 14 are mounted. Electrode 14 is in the form of an annular band which may fit within a suitable groove in the wall of the holder 10. The spiral electrode 12 extends from the forward portion of the holder 10 and may be attached to the fetus by rotating the electrode assembly, causing the spiral to "screw" into the fetal presenting part (generally the scalp). Wires 16 and 18, attached to the respective electrodes 12 and 14, extend through the back of the plastic holder 10 and (during use) are connected to the measuring circuitry described below with respect to FIG. 2.

In the preferred embodiment, the electrode head shown in FIG. 1 is intended to be applied in the same way as the fetal heart rate electrode illustrated in FIGS. 8–10 of U.S. Pat. No. Re. 28,990 of Hon. The principal structural difference between the electrode of FIG. 1 and that shown in FIGS. 8–10 of U.S. Pat. No. Re. 28,990 is that the maternal plate electrode of the patent has been replaced with the band 14 for reasons explained below. The device itself may be applied in the same manner using a curved guide tube 20 and relatively flexible drive tube 22 as described in the reissue patent. Where the secondary or maternal electrode comprises a band as shown in FIG. 1, a rear fin 23, integrally formed with holder 10, may be provided to engage slots 24 of the driving tube to enable the doctor to rotate the electrode assembly.

For the purposes of clarity and simplicity, driving tube 22 and guide tube 20 have not been shown in full detail in FIG. 1. To the extent a description of these elements and the method of attachment of the electrode may be required to understand the invention, U.S. Pat. No. Re. 28,990 is hereby incorporated by reference into this specification.

When the electrode assembly shown in FIG. 1 is attached to the fetus, the spiral electrode 12 engages the fetal tissue whereas the maternal or secondary electrode 14 will contact the amniotic fluids of the mother. Each of electrodes 12 and 14 must be made of an electrode material which, in the presence of hydrogen ions will generate an electromotive force. In addition, the spiral electrode 12 must have sufficient structural integrity to serve as an attachment means to the fetus.

The electrodes may be made of a variety of different materials, but, in the presently preferred embodiment of the invention, each of the electrodes 12 and 14 comprises a stainless steel wire which is silver plated and then chloridized to provide a silver-silver chloride electrode. As is well-known, silver-silver chloride in the presence of hydrogen (and others) ions will generate a readily measured electromotive force. Although a potential difference will also arise because of the presence of chloride ions, this will not prevent the operation of the invention in its intended fashion so long as the concentration of chloride ions at both electrodes does not change with time during the delivery. Moreover, it is not necessary that the pH values of the fetus and mother be the same as long as there is no substantial change in pH value of the mother during birth. Under these conditions, any change in potential difference can be safely assumed to be due to the fetus.

Instead of a band, electrode 14 may take the form of a plate extending from the rear surface of holder 10, as shown in U.S. Pat. No. Re. 28,990. However, it is more difficult to silver plate a flat electrode of this type, and improper silver plating can result in drifting during use.

The electrode assembly shown in FIG. 1 may be used to measure both fetal heart rate and pH values. Since the electronic circuitry for measuring both pH values and fetal heart rate is conventional, these devices are shown in block diagram form only in FIG. 2.

With the mother grounded, the output from the two electrodes is coupled to a differential amplifier 30 which produces a voltage when there is a voltage difference across the two half cells. This difference voltage is amplified by amplifier 32 to provide an output voltage representative of a change in hydrogen ion concentration in the fetus (i.e., a change in pH). The amplitude of this voltage may be recorded on a standard strip chart recorder (not shown) to provide a continuous indication of changes of fetal pH values. In accordance with the invention, changes can be reflected in about ten seconds as opposed to thirty to forty seconds in the case of the glass electrode of the Moller patent.

Amplifier 32 may be a D.C. amplifier with an upper cut-off frequency of about ten (10) cycles per minute.

The output of the amplifier 30 may be coupled via an A.C. coupling circuit 34 to a filter 36 which produces a signal corresponding to the fetal EKG as explained in U.S. Pat. No. Re. 28,990. This signal may then be used in conventional fashion to provide an indication of fetal heart rate which, typically, is also recorded (along with an indication of intrauterine contractions) on a strip chart recorder.

The invention has been described in terms of the measurement of changes in pH values of the fetus. In fact, the electrode measures changes in hydrogen ion concentration which also represents the partial pressure of carbon dioxide ($PCO_2$) in the partial blood. Insofar as the invention is concerned, it is only significant that the measurement of the change in hydrogen ion concentration can be correlated to fetal well-being. It may even be the case that the electrode is responsive to ions of elements other than hydrogen, the important factor being that the output of the electrode does provide meaningful information. Reference herein to the measurement of changes in "pH values" is thus intended to include the measurement of a change in the concentration of an ion in the fetal tissue which may be correlated to the condition of the fetus.

What is claimed is:

1. Apparatus for use in measuring continuously the change of pH of a fetus, comprising
    a holder made of an insulating material,
    a first electrode extending from the forward end of said holder and shaped to attach to the fetus during delivery to secure said first electrode thereto, said first electrode consisting of a solid material which, in the presence of hydrogen ions, will form a first half cell,
    a second electrode secured to said holder and consisting of a material which, in the presence of hydrogen ions, will form a second half cell, said second electrode being spaced on said holder relative to said first electrode so as to respond to maternal pH values,
    and means responsive to the difference between the voltages produced by said first and second half cells for continuously measuring the changes in pH of the fetus.

2. Apparatus according to claim 1, wherein said first electrode comprises a spiral adapted to be screwed into the fetus.

3. Apparatus according to claim 2, wherein said second electrode comprises a band extending at least partly around the circumference of said holder.

4. Apparatus according to any of claims 1, 2 or 3, wherein said first and second electrodes comprise electrically conductive material, and including means connected to said first and second electrodes for producing a signal representative of fetal heart rate.

5. Apparatus according to any of claims 1, 2 or 3 wherein each of said electrodes comprises plated stainless steel.

6. An electrode assembly for use in measuring continuously the change in pH values of a fetus, comprising:
a holder made of a dielectric material,
a first electrode extending from the forward end of said holder, said electrode comprising a stainless steel spiral having coated thereon material which, in the presence of hydrogen ions, will form a first half cell,
a second electrode supported on said holder and spaced from said spiral electrode, said second electrode including material which, in the presence of hydrogen ions, will form a second half cell, and
wires connected to said first and second electrodes for enabling the measurement of the potential difference between said first and second half cells for continuously measuring the change in pH value of the fetus.

7. A fetal electrode according to claim 6, wherein said second electrode is made of stainless steel having coated thereon said second electrode material.

* * * * *